(12) United States Patent
Shen et al.

(10) Patent No.: US 11,331,387 B2
(45) Date of Patent: May 17, 2022

(54) SELF-ASSEMBLED DRUG-LOADING SYSTEM AND PREPARATION METHOD THEREFOR

(71) Applicant: SHANGHAI SELECTION BIOSCIENCE LLC., Shanghai (CN)

(72) Inventors: Youqing Shen, Zhejiang (CN); Shiqi Hu, Zhejiang (CN)

(73) Assignee: SHANGHAI BEST-LINK BIOSCIENCE, Shanghai (CN)

(*) Notice: Subject to any disclaimer, the term of this patent is extended or adjusted under 35 U.S.C. 154(b) by 0 days.

(21) Appl. No.: 16/467,641

(22) PCT Filed: Dec. 14, 2017

(86) PCT No.: PCT/CN2017/116061
§ 371 (c)(1),
(2) Date: Jun. 7, 2019

(87) PCT Pub. No.: WO2018/103759
PCT Pub. Date: Jun. 14, 2018

(65) Prior Publication Data
US 2019/0336604 A1  Nov. 7, 2019

(30) Foreign Application Priority Data
Dec. 7, 2016 (CN) .......................... 201611156250.X

(51) Int. Cl.
*A61K 41/00* (2020.01)
*A61K 9/51* (2006.01)
(Continued)

(52) U.S. Cl.
CPC ........ *A61K 41/0057* (2013.01); *A61K 9/5192* (2013.01); *A61K 31/12* (2013.01);
(Continued)

(58) Field of Classification Search
CPC .. A61K 41/0057; A61K 9/5192; A61K 31/12; A61K 31/337; A61K 31/4745;
(Continued)

(56) References Cited

U.S. PATENT DOCUMENTS

2011/0286915 A1* 11/2011 Lam .................. A61P 35/00
424/1.29
2012/0225017 A1   9/2012 Gombotz

FOREIGN PATENT DOCUMENTS

CN  103951766 A   7/2014
CN  104984340 A  10/2015

OTHER PUBLICATIONS

Dinarvand et al., Polylactide-co-glycolide nanoparticles for controlled delivery of anticancer agents, 2011, International Journal of Nanomedicine, 2011:6, 877-895. (Year: 2011).*
(Continued)

*Primary Examiner* — Trevor Love
(74) *Attorney, Agent, or Firm* — Harness, Dickey & Pierce, P.L.C.

(57) ABSTRACT

Disclosed are a self-assembled drug-loading system containing a hydrophilic phototherapeutic drug and a hydrophobic chemotherapeutic drug, a preparation method therefor and the use thereof for preparing an anti-tumor drug. The self-assembled drug-loading system is a water-soluble complex or water-dispersible nanoparticles formed by means of π-π interaction or hydrophobic interaction between the phototherapeutic drug and the chemotherapeutic drug, wherein the molar ratio of the phototherapeutic drug to the chemotherapeutic drug is 2:1 to 1:10.

9 Claims, 10 Drawing Sheets

(51) Int. Cl.
    *A61K 31/12*     (2006.01)
    *A61K 31/337*     (2006.01)
    *A61K 31/4745*     (2006.01)
    *A61K 9/14*     (2006.01)
    *A61P 35/00*     (2006.01)
    *A61K 45/06*     (2006.01)
    *A61K 9/19*     (2006.01)

(52) U.S. Cl.
    CPC ........ *A61K 31/337* (2013.01); *A61K 31/4745* (2013.01); *A61K 41/0071* (2013.01); *A61P 35/00* (2018.01)

(58) Field of Classification Search
    CPC ...... A61K 41/0071; A61K 9/14; A61K 45/06; A61K 9/19; A61P 35/00
    See application file for complete search history.

(56) References Cited

OTHER PUBLICATIONS

Mingbin Zheng et al., "Single-step assembly of DOX/ICG loaded lipid-polymer nanoparticles for highly effective chemo-photothermal combination therapy", ACS Nano, vol. 7, No. 3, 2013, pp. 2056-2067.

Cheng-Liang Peng et al., "Dual chemotherapy and photodynamic therapy in an HT-29 human colon cancer xenograft model using SN-38-loaded chlorin-core star block copolymer micelles", Biomaterials, vol. 30, No. 21, 2009, pp. 3614-3625.

Ruiyun Zhang et al., "Carrier-free, chemophotodynamic dual nanodrugs via self-assembly for synergistic antitumor therapy", ACS Appl. Mater. Interfaces, vol. 8, No. 21, 2016, pp. 13262-13269.

International Search Report and Written Opinion of PCT/CN2017/116061 dated Mar. 14, 2018.

* cited by examiner

SELF-ASSEMBLED DRUG-LOADING SYSTEM AND PREPARATION METHOD THEREFOR

CROSS REFERENCE TO RELATED APPLICATIONS

This application is a U.S. National Phase Application under 35 U.S.C. 371 of International Application No. PCT/CN2017/116061 filed on Dec. 14, 2017. This application claims priority to Chinese Application No. 201611156250.X filed on Dec. 7, 2016. The entire disclosures of all of the above applications are incorporated herein by reference.

FIELD OF INVENTION

The present invention relates to biomedical field, in particular to a self-assembled drug-loading system and a preparation method therefor.

PRIOR ARTS

Photodynamic therapy (PDT) utilizes certain dyes (photosensitizers) that can produce superoxide radicals or heat upon light absorption to kill tumor cells, thus achieve anti-tumor effects. It is a new technology which was emerged and has been developing over the last two decades for the treatment of cancer in clinical medicine. Compared with conventional tumor treatment methods such as surgery, chemotherapy and radiotherapy, PDT only takes action in the local part of light irradiation. Therefore, the system has little toxicity and side effects, and is especially suitable for the special patients who are frail and inoperable.

The property of the photosensitizer directly determines the efficacy of PDT. The current photosensitizers can be classified according to their chemical structure and composition: (1) porphyrin compounds, such as 5-aminolevulinic acid (ALA), Chlorin e6, benzoporphyrin monoacid ring and the like; (2) chlorophyll compounds, such as chlorin compounds, purpurin compounds and bacteriochlorin compounds; (3) dyes, such as phthalocyanine compounds, naphthalocyanine compounds and the like. Among them, indocyanine green (ICG), as a near-infrared absorbing drug, is an amphiphilic tricarbonyl near-infrared absorbing dye. It has been approved by the US Food and Drug Administration (FDA) for human clinical disease diagnosis and medical imaging, and has also been included in the Chinese Pharmacopoeia for diagnostic use. Its maximum absorption wavelength is around 800 nm, which has a good tissue penetration depth, making it a promising photosensitizer. However, ICG is prone to deterioration upon light or heat, and is unstable and easy to aggregate in aqueous solution. It is also rapidly eliminated in vivo due to the tendency to combine with plasma proteins in the body. These shortcomings restrict the prevalent application of ICG as a photosensitizer. In order to solve the above problems of ICG, researchers prepared ICG nanoparticles by using polyacrylamide, calcium silicate phosphate and lipid polymer to improve its stability. The long circulation and passive targeting characteristics of the nanoparticles improve ICG's blood circulation time and enrichment in tumor. For example, a nano-delivery system prepared by folic acid-mediated PLGA-encapsulated ICG can stabilize ICG and better target the tumor sites.

The efficacy of treating cancer by PDT alone is often limited. However, in addition to generating a series of oxidation reactions and heat via photochemical reaction, the biological mechanism of photodynamic anti-tumor effect also includes action on the microvessels of the tumor sites, which results in complete closure of blood vessels, and the tumor tissue is necrotic due to hypoxia and nutrient depletion. Moreover, it can stimulate the participation of the immune system and promote the release of cytokines such as prostaglandins, lymphokines and thromboxane. The combination of PDT with the traditional chemotherapeutic drugs will not increase the side effects of the chemotherapeutic drugs. Instead, the photodynamic therapy can overcome the drug resistance caused by chemotherapy through different mechanisms. Therefore, the application of PDT in the combination therapy is a promising strategy. Researches have shown that PDT combined with the chemotherapeutic drugs such as Cisplatin, Doxorubicin, CPT11, etc., have synergistic anti-tumor effects and improved efficacy. Tayyaba Hasan et al. carried out the combination therapy experiments using porphyrins photosensitizers and Irinotecan liposomes in a pancreatic cancer model, the tumor inhibition rate was as high as 70% after 3-week of treatment, and the inhibition rate was only 25% when the two methods were used alone. Zheng et al. found that the phototherapy and chemotherapy of the PLGA-lipid nanoparticles co-loaded with Doxorubicin and ICG produce a remarkably synergistic effect on the inhibition of the tumor cells. Therefore, the combination of the phototherapy and the chemotherapy will be a clinically transformable and effective approach.

However, how to effectively prepare clinically transformable photosensitizers and chemotherapeutic drug formulations is the key to achieve the combination therapy. The current method is to co-load a chemotherapeutic drug and a photosensitizer into a delivery carrier such as a liposome or a nanoparticle. For example, Zheng et al. (*Single-step assembly of DOX/ICG loaded lipid—polymer nanoparticles for highly effective chemo photothermal combination therapy. ACS Nano*, 2013. 7(3): p. 2056-67) prepared a PLGA lipid nanosystem co-loaded with Doxorubicin and indocyanine green. Shieh et al. (*Dual chemotherapy and photodynamic therapy in an HT-29 human colon cancer xenograft model using SN-38-loaded chlorin-core star block copolymer micelles. Biomaterials,* 2009. 30(21): p. 3614-25) found that a combination of chemotherapy and phototherapy using polyethylene glycol-polycaprolactone micelle co-loaded with SN38 and chlorin could achieve good in vivo effects. Moreover, other patent documents such as US2012225017A1 disclosed a micelle formed by PEO-PHB-PEO and PEO-PPO-PEO copolymer material; the copolymer material was self-assembled into micelle in an aqueous solution, and the micelle also contain Camptothecin or a derivative thereof and indocyanine green. Patent document CN103951766A disclosed a photoresponse micelle based on a polymer resulting from hyaluronic acid and an o-nitrobenzyl alcohol derivative.

However, current techniques inevitably utilized copolymer for simultaneous loading of the two drugs, either in the form of liposome or nanoparticle, which complicates the drug-loading process, the drug-loading system, and the product quality control, resulting in difficulty in clinical transformation.

Content of the Present Invention

In order to overcome the deficiencies of the prior art, the present invention provides a novel self-assembled drug-loading system, a preparation method therefor and a use thereof.

The first object of the present invention is to provide a self-assembled drug-loading system, and the technical solution provided by the present invention is as follows:

A self-assembled drug-loading system, comprising a hydrophilic phototherapeutic drug and a hydrophobic chemotherapeutic drug.

Preferably, the self-assembled drug-loading system is formed by a direct interaction between the hydrophilic phototherapeutic drug and the hydrophobic chemotherapeutic drug.

Preferably, the hydrophilic phototherapeutic drug interacts with the hydrophobic chemotherapeutic drug to form a water-soluble complex or water-dispersible nanoparticles.

Preferably, the molar ratio of the hydrophilic phototherapeutic drug to the hydrophobic chemotherapeutic drug in the self-assembled drug-loading system is from 2:1 to 1:10.

Preferably, there are varying degrees of π-π interaction or hydrophobic interaction between the hydrophilic phototherapeutic drug and the hydrophobic chemotherapeutic drug.

Further preferably, the hydrophilic phototherapeutic drug is a photosensitizer with a planar conjugated structure.

The photosensitizer is, for example, porphyrin compounds, chlorophyll compounds, phthalocyanine compounds or indocyanine green with a planar conjugated structure;

For example, the structure of the porphyrin-derived Verteporfin is as follows:

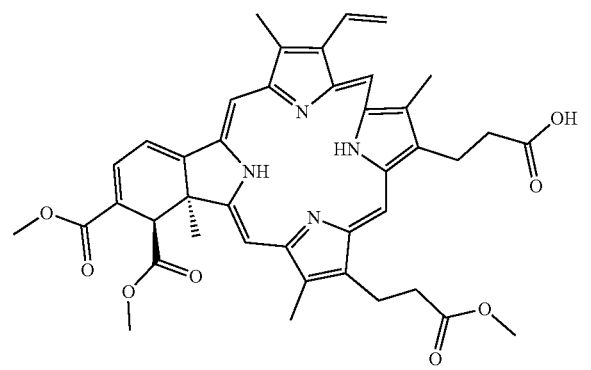

The structure of the chlorophyll-derived Chlorin e6 is as follows:

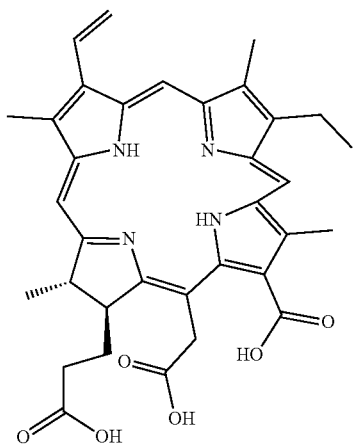 [SMILES: C=Cc1c(C)c2cc3nc(c(CC(=O)O)c4[nH]c(cc5nc(cc1[nH]2)C(C)=C5CC)c(C)c4C(=O)O)[C@@H](CCC(=O)O)[C@@H]3C]

Further preferably, in terms of the light penetration depth, ICG shows maximum absorption around the wavelength of 800 nm, and light source with such wavelength exhibits good tissue penetration ability. Moreover, ICG has been clinically applied. Therefore, ICG is a preferred model drug, and the structure of ICG is as follows:

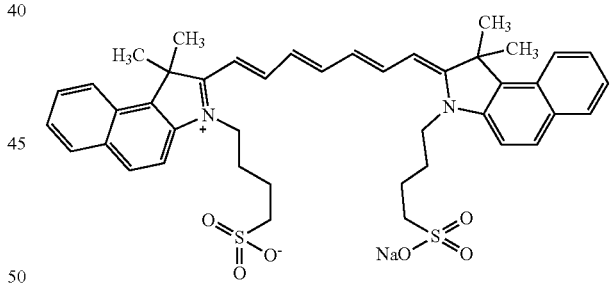

Further preferably, the hydrophobic chemotherapeutic drug contains phenyl ring structure and can be camptothecin compounds, taxanes, curcumin compounds, doxorubicin, 8-hydroxyquinoline or the like.

The camptothecin compounds include: camptothecin, 7-ethyl-10-hydroxycamptothecin (SN38), irinotecan, 9-aminocamptothecin, 9-nitrocamptothecin and the like; preferably camptothecin, 7-ethyl-10-hydroxycamptothecin (SN38). The partial structure of the camptothecin compounds is:

![structure](camptothecin core structure)

| Analogues | $R_1$ | $R_2$ | $R_3$ | $R_4$ |
|---|---|---|---|---|
| 1(Topotecan) | H | OH | $CH_2N(CH_3)_2$ | H |
| 2(Irinotecan) | H | OCO—N(piperidine)-N(piperidine) | H | Ethyl |
| 3(SN-38) | H | OH | H | Ethyl |
| 4(9-aminoCPT, 9-AC) | H | $NH_2$ | H | H |
| 5(Rubitecan) | H | $NO_2$ | H | H |
| 6(Lurotecan, CI141721, CG211) | | O—CH$_2$CH$_2$—O | $H_2C$—N(piperazine)N—$CH_3$ | H |
| 7(Exatecan, DX-89521f) | H | H | H | H |
| 8(Silatecan, DB-67) | H | OH | H | Si(tBu)(CH$_3$)$_2$ |
| 9(Karetineein, BNP-1350) | H | H | H | $CH=NOC(CH_3)_3$ |
| 10(Gimatecan, ST-1481) | H | H | H | $CH_2CHNHC(CH_3)_2$ |
| 11(CKD-602) | H | H | H | $CH_2CHSi(CH_3)_3$ |

The taxanes mainly include: paclitaxel (PTX), docetaxel (DTX), cabazitaxel, larotaxel and the like; preferably paclitaxel.

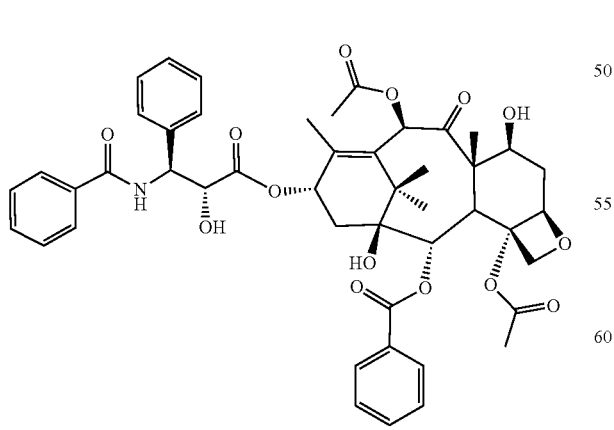

Paclitaxel

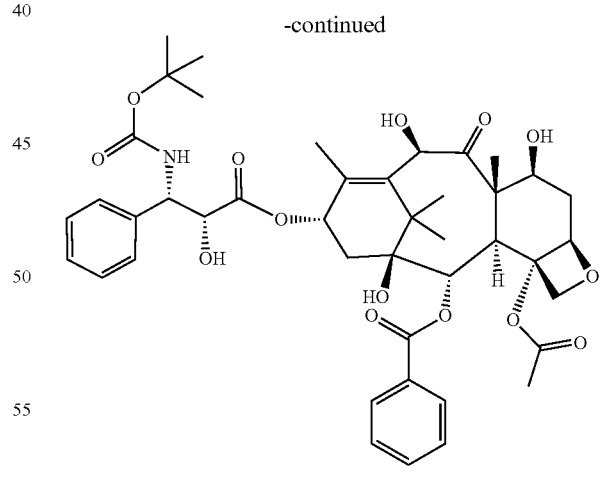

Docetaxel

The curcumin compounds include: curcumin, demethoxycurcumin, and bisdemethoxycurcumin. The structure of the curcumins is as follows:

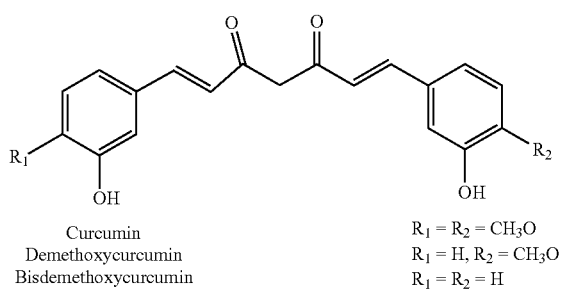

| | |
|---|---|
| Curcumin | $R_1 = R_2 = CH_3O$ |
| Demethoxycurcumin | $R_1 = H, R_2 = CH_3O$ |
| Bisdemethoxycurcumin | $R_1 = R_2 = H$ |

From the viewpoint of chemotherapeutic drugs, it is universal to directly solubilize a hydrophobic chemotherapeutic drug with a hydrophilic phototherapeutic drug, when there is strong π-π interaction or hydrophobic interaction between the hydrophilic phototherapeutic drug with a conjugated group and the chemotherapeutic drug molecule containing a similar conjugated group. Compared with the conventional self-assembled drug-loading system that improves the solubility of the hydrophobic chemotherapeutic drug by the hydrophilicity of a surfactant, the usage amount of the hydrophilic phototherapeutic drug is less. On the other hand, chemotherapy and photodynamic therapy can be simultaneously performed to achieve synergistic treatment effect in the case of the self-assembled drug-loading system formed by a hydrophilic phototherapeutic drug and a hydrophobic chemotherapeutic drug.

Further, the self-assembled drug-loading system of the present invention can be formed without the addition of a surfactant or a polymer. The composition of the system is very simple, and it may even include only two ingredients: a hydrophilic phototherapeutic drug and a hydrophobic chemotherapeutic drug. The addition amount of the hydrophilic phototherapeutic drug is much reduced, and the synergistic effect of chemotherapy and photodynamic therapy is more significant.

The highly hydrophobic chemotherapeutic drugs which are capable of interacting with the photosensitizer ICG for solubilization include: curcumin compounds, taxanes, camptothecin compounds, 8-hydroxyquinoline and the like. A water-soluble complex is formed by the combination of ICG with a drug of low crystallinity such as curcumin compounds or taxanes. Nanoparticles are formed by the combination of ICG with a drug of high crystallinity such as camptothecin compounds. The formation of the water-soluble complex or the nanoparticles are realized via self-assembly.

The second object of the present invention is to provide a preparation method for the above-described self-assembled drug-loading system, comprising the following steps:

(1) dissolving the water-soluble phototherapeutic drug and the hydrophobic chemotherapeutic drug in an organic solvent.

(2) adding an aqueous solution.

Preferably, the organic solvent is selected from the group consisting of DMSO, DMF, THF, methanol, ethanol and isopropanol.

Preferably, the aqueous solution is selected from the group consisting of pure water, physiological saline, 5 wt. % glucose solution and phosphate buffer.

The third object of the present invention is to provide a preparation method for a complex preparation comprising a water-soluble phototherapeutic drug and a hydrophobic chemotherapeutic drug, comprising the steps of:

(1) dissolving the water-soluble phototherapeutic drug and the hydrophobic chemotherapeutic drug in an organic solvent.

(2) adding an aqueous solution to form a water-soluble complex or nanoparticles.

(3) removing the organic solvent to obtain an aqueous solution formulation or further lyophilizing to prepare a lyophilized powder formulation.

Preferably, the organic solvent is selected from the group consisting of DMSO, DMF, THF, methanol, ethanol and isopropanol.

Preferably, the aqueous solution is selected from the group consisting of pure water, physiological saline, 5 wt. % glucose solution and phosphate buffer.

The fourth object of the present invention is to provide a use of the above-described self-assembled drug-loading system in manufacturing a medicament for treating tumor; or a method for treating tumor using the above-described self-assembled drug-loading system.

The present invention has the following beneficial effects:

(1) From the viewpoint of water-soluble phototherapeutic drugs, the quenching phenomenon caused by the aggregation of water-soluble phototherapeutic drugs such as photosensitizers in aqueous solution is the main reason for the poor photosensitivity. In the present invention, upon mixing, the water-soluble phototherapeutic drugs are separated from each other by the hydrophobic chemotherapeutic drugs, which increases the distance between the photosensitizer molecules. It thereby suppresses the quenching thereof and enhances the photosensitizing effect, consequently strengthens its photothermal and photodynamic therapy effects. Meanwhile, it can reduce the aggregation of indocyanine green, prolong the circulation time in the body and improve the bioavailability thereof.

(2) The water-soluble phototherapeutic drugs mostly possess a planar conjugated structure, including chlorophyll compounds, phthalocyanine dyes and indocyanine green, and display varying degrees of π-π interaction and hydrophobic interaction with the hydrophobic chemotherapeutic drugs containing phenyl ring structure. The examples of the present invention indicate that water-soluble phototherapeutic drugs are capable of solubilizing the hydrophobic drugs, thereby solving the problem in the administration of the hydrophobic drugs.

(3) The self-assembled drug-loading system and the complex formulation of the present invention can be used in combination therapy of phototherapy and chemotherapy. In vitro and in vivo results revealed remarkable effects and advantages of the combination therapy.

(4) Most importantly, the preparation process of the present invention is simple and facile, which can be carried out without the addition of a surfactant or the introduction of a polymer. Furthermore, the prepared self-assembled drug-loading system only consists of two ingredients: a hydrophilic phototherapeutic drug and a hydrophobic chemotherapeutic drug.

The method provided by the present invention is that: a hydrophilic phototherapeutic drug forms a water-soluble complex or nanoparticles with a hydrophobic drug comprising similar structure. Specifically, it forms the water-soluble complex with the hydrophobic drug of low crystallinity, and forms the nanoparticles of good dispersity with the hydrophobic drug of high crystallinity. The formation of the water-soluble complex and complex nanoparticles is a self-assembled process. It constitutes the self-assembled drug-loading system, and the preparation process therefor is simple. The complex formulation thereof may include aqueous solution of the complex, complex nanoparticles or the lyophilized powder formulation. It has been proved by a large number of experiments that the self-assembled drug-loading system and the complex formulation of the present invention can not only improve the phototherapy effect of the photosensitizer, but also solve the problem of the administration of the water-insoluble chemotherapeutic drugs. Compared to monotherapy, the present system realizes combination therapy and exhibit a significantly improved efficacy.

The self-assembled drug-loading system and the complex formulation thereof of the present invention embraces various advantages such as simple drug-loading process, succinct drug-loading system and superior quality control, which renders the clinical transformation much more feasible. The characterization of the formulation and a series of in vitro and in vivo experiments of the present invention prove that the self-assembled drug-loading system and the complex formulation of the present invention show good combined therapeutic effect on tumors, and can effectively treat breast cancer, prostate cancer, ovarian cancer, intestinal cancer, lung cancer and the like.

The self-assembled drug-loading system of the present invention can be administered by injection, and can be prepared into a lyophilized powder formulation. In addition, the dosage can be determined by those skilled in the art according to the dosage of the prior anti-tumor drug, and adjusted according to the individual situation.

DETAILED DESCRIPTION OF THE PREFERRED EMBODIMENTS

Figure 1:
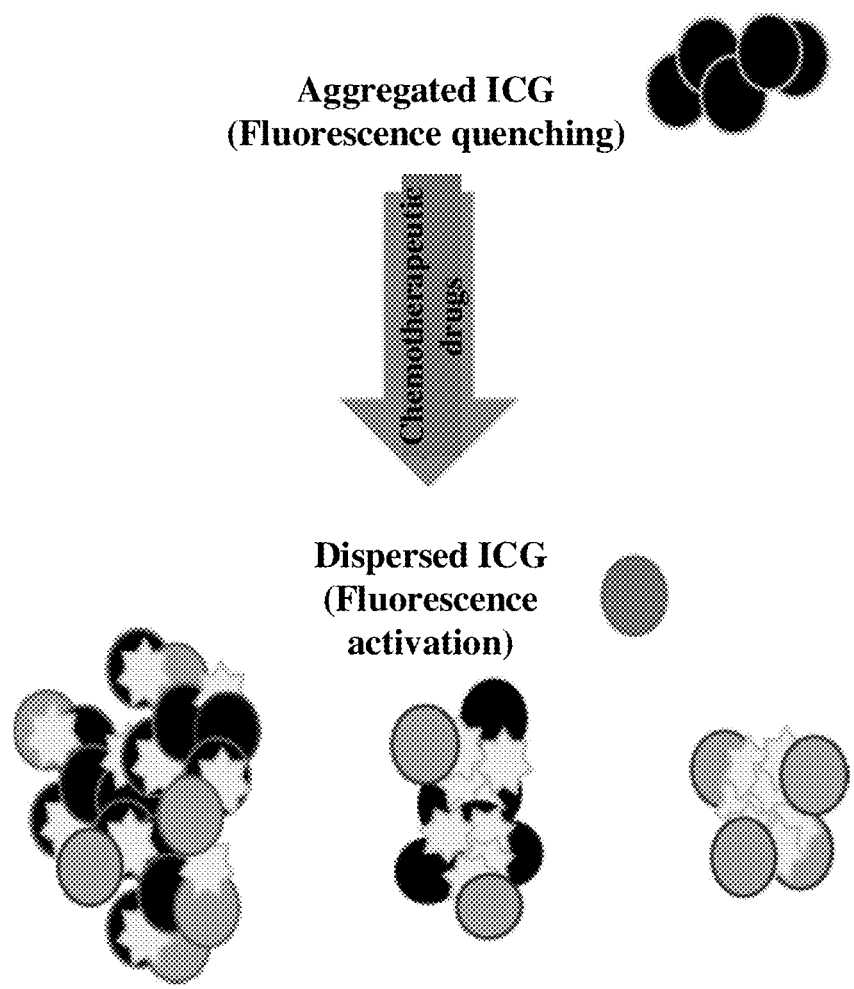
FIG. 1 is a process schematic diagram of forming a complex or complex nanoparticles by a hydrophilic phototherapeutic drug and a hydrophobic chemotherapeutic drug.

The present invention provides specific embodiments, but the present invention is not limited thereto. Several modifications can be made by those skilled in the art, which are also considered within the protection scope of the present invention.

Embodiments 1

A method for preparing ICG/SN38 complex nanoparticles, comprising the following steps:

(1) Dissolving indocyanine green ICG and the chemotherapeutic drug SN38 in an organic solvent in a certain ratio, specifically, dissolving I1S2 (the molar ratio of ICG to SN38 was 1:2, ICG was 0.775 mg, SN38 was 0.78 mg), I1S1 (the molar ratio of ICG to SN38 was 1:1, ICG was 0.775 mg, SN38 was 0.39 mg), I2S1 (the molar ratio of ICG to SN38 was 2:1, ICG was 0.775 mg, SN38 was 0.195 mg), I1S5 (the molar ratio of ICG to SN38 was 1:5, ICG was 0.775 mg, SN38 was 1.95 mg) and I1S10 (the molar ratio of ICG to SN38 was 1:10, ICG was 0.775 mg, SN38 was 3.9 mg) in 20 µL of DMSO, respectively.

(2) Adding 1 mL of pure water to the above solution to obtain different ratios of indocyanine green/SN38 complex nanoparticle dispersion.

(3) Placing the above nanoparticle dispersion in an ultracentrifugal filter tube (3K), washing three times with pure water to wash away the organic solvent DMSO and small molecule ICG and drying.

In addition to DMSO, the organic solvent can be selected from the group consisting of THF, acetonitrile, DMSO and DMAC.

A series of nanoparticles with different ratios of ICG to SN38 were prepared in embodiment 1, and the molar ratios were 2:1, 1:1, 1:2, 1:5, 1:10, i.e., I2S1, I1S1, I1S2, I1S5, I1S10, respectively.

Figure 2:
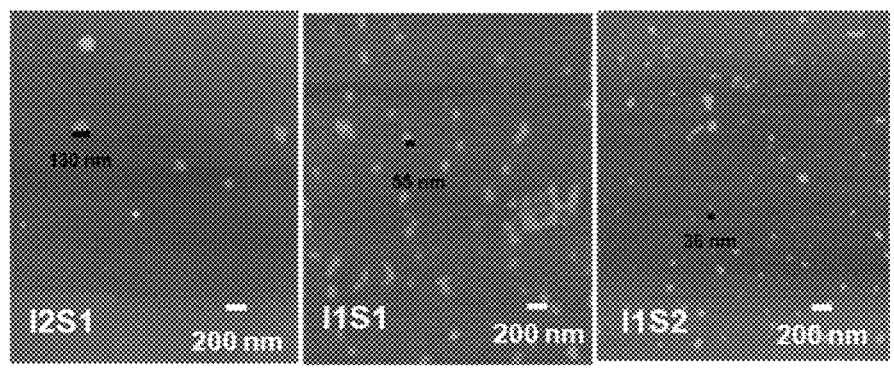
FIG. 2 is an atomic force microscopy image of ICG/SN38 nanoparticles. From left to right, the molar ratio of ICG to SN38 is 2:1, 1:1 and 1:2, and the scale is 200 nm.

From the results of the DLS analysis in FIG. 2, when a small amount of SN38 was added, it served as aggregated nuclei for ICG, and the complex assembled as large particles with the size of about 130 nm; when more SN38 was added, the interaction between SN38 and ICG was strengthened, thereby forming stable nanoparticles in a smaller particle size, wherein I1S1 is about 55 nm, and I1S2 is only about 36 nm.

In addition to SN38, we found that the complex nanoparticles were also formed by indocyanine green with other camptothecin drugs such as irinotecan, topotecan, camptothecin and the like; similar nanoparticles were also observed by combination of indocyanine green with doxorubicin or 8-hydroxyquinoline.

Embodiment 2

A method for preparing an aqueous solution of ICG/PTX complex, comprising the following steps:

(1) Dissolving indocyanine green ICG and Paclitaxel PTX in an organic solvent in a certain ratio, specifically, dissolving I1P1 (the molar ratio of ICG to PTX was 1:1, ICG was 0.775 mg, PTX was 0.854 mg), and I2P1 (the molar ratio of ICG to PTX was 2:1, ICG was 0.775 mg, and PTX was 0.427 mg) in 20 μL of ethanol, respectively.

(2) Adding 1 mL of 5% dextrose solution to the above solution, and removing the organic solvent by rotary evaporation under reduced pressure to obtain different indocyanine green/paclitaxel complex formulations.

In addition to ethanol, the organic solvent can be selected from the group consisting of methanol, isopropanol and acetonitrile.

In addition to paclitaxel, the hydrophobic drugs can be curcumin, 8-hydroxyquinoline and the like. All complex formulations thereof can be prepared by a similar method according to embodiment 2. Indocyanine green can effectively solubilize these hydrophobic substances. It is speculated that the hydrophobic drugs were filled between the two claws of indocyanine green, forming a structure similar to a coordination complex to some extent, thereby being well dissolved in water.

Embodiment 3

A method for preparing an aqueous solution of ICG/CCM complex, comprising the following steps:

(1) Dissolving indocyanine green ICG and Curcumin CCM in an organic solvent in a certain ratio, specifically, dissolving I1C2 (the molar ratio of ICG to CCM was 1:2, ICG was 0.775 mg, and CCM was 1.71 mg), I1C10 (the molar ratio of ICG and CCM was 1:10, ICG was 0.775 mg, and CCM was 8.55 mg) in 20 μL of ethanol, respectively.

(2) Adding 1 mL of physiological saline to the above solution, and removing the organic solvent by rotary evaporation under reduced pressure to obtain a different indocyanine green/Curcumin complex formulation.

Figure 4:
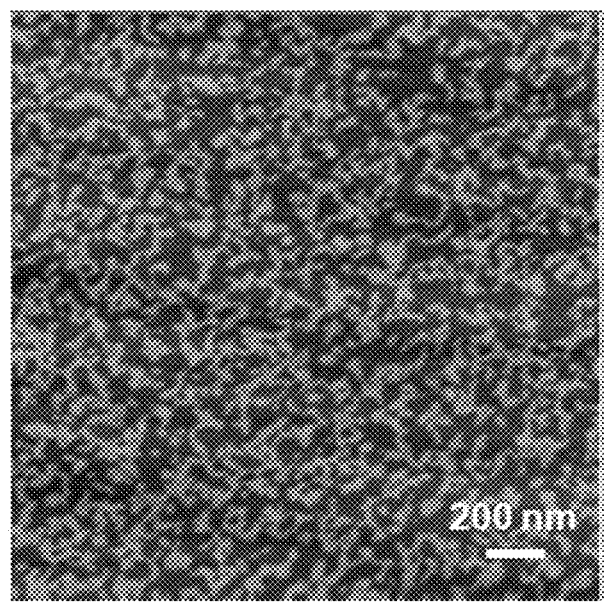
FIG. 4 is an atomic force microscopy image of the aqueous solution prepared by ICG and Curcumin.

It has been shown that the particle size was undetectable in the solution formed by indocyanine green and curcumin, which meant complete dissolution in water. The solution formed uniformly dispersed water spots after dried on the mica flakes (FIG. 4).

Embodiment 4

A method for preparing Chlorin e6/SN38 complex nanoparticles comprises the following steps:

Dissolving Chlorin e6 and the chemotherapeutic drug SN38 in an organic solvent in a certain ratio, specifically, dissolving I1E2 (the molar ratio of Chlorin e6 to SN38 was 1:2; Chlorin e6 was 1.438 mg; SN38 was 0.784 mg) or I1E10 (the molar ratio of chlorin e6 to SN38 was 1:10; ICG was 1.438 mg; CCM was 3.92 mg) in 25 μL of DMF, adding 2 mL of 5% glucose solution under ultrasound irradiation and obtaining the nanoparticles by nano co-precipitation.

Figure 3:
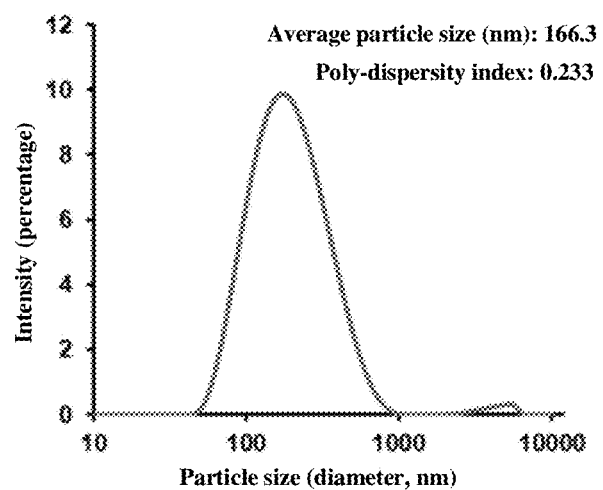
FIG. 3 is a dynamic light scattering particle size distribution diagram of the nanoparticles formed by the interaction of Chlorin e6 and SN38.

SN38 is highly crystalline and could induce strong conjugation with the delocalized 7C ring of Chlorin e6. These factors facilitate the formation of nanoparticles between SN38 and Chlorin e6. As shown in FIG. 3, the size of I1E2 nanoparticle was measured to be around 166 nm. The applicant has demonstrated through extensive experiments that other photosensitizers equipped with a porphyrins-structure can also interact with chemotherapeutic drugs such as SN38 to form nanoparticles.

FIG. 1 is a process schematic diagram of forming a complex or complex nanoparticles by a hydrophilic phototherapeutic drug and a hydrophobic chemotherapeutic drug. The hydrophilic photosensitizer such as indocyanine green or Chlorin e6 forms loose aggregates to some extent in aqueous solution. When hydrophobic anticancer drug of high crystallinity such as SN38 is added, it is easy to form a hydrophobic core, thereby forming nanoparticles; when indocyanine green and hydrophobic anticancer drugs of low crystallinity such as paclitaxel or curcumin are mixed, they are superimposed to form a water-soluble complex, thereby solubilizing the hydrophobic drugs.

Embodiment 5: Preparation of ICG Solution (1) Dissolving 0.775 mg of indocyanine green ICG in 20 μL of ethanol.

(2) Adding 1 mL of 5% dextrose solution to the above solution, and removing the organic solvent by rotary evaporation under reduced pressure to obtain ICG solution.

The products prepared in embodiments 1-5 were used for testing in the following application embodiments.

Figure 5:
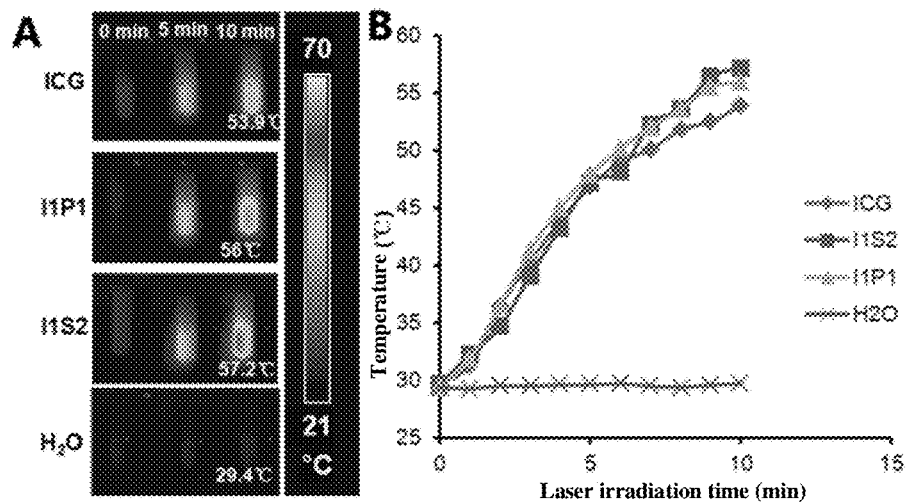
FIG. 5 is a graph showing the changes in the photothermal temperature of different ICG formulations under continuous irradiation with the 808 nm laser.

Application Embodiment 1: Photothermal Effect of the Indocyanine Green Complex Formulation at the Solution Level The in vitro photothermal effect of the above formulation was recorded by a FLTR-S65 infrared imaging camera. As shown in FIG. 5, being continuously irradiated with an 808 nm wavelength laser, the temperature of the ICG solution was raised from 29.7° C. to 53.9° C., and the temperature of the ICG/PTX (I1P1) solution was raised from 29.4° C. to 56° C., while the temperature of the ICG/SN38 (I1S2) nanoparticles was raised from 29.7° C. to 57.2° C., indicating that after the formation of complex, the photothermal effect of ICG was improved rather than weakened.

Application Embodiment 2: Photodynamic Effect of the Indocyanine Green Complex Formulation at the Solution Level The production of singlet oxygen is a key step in photodynamic therapy. Therefore, the ability of reactive oxygen species (ROS) production was compared among ICG/SN38 nanoparticles (I1S2), ICG/PTX complex aqueous solution (I1P1) and ICG solution under 808 nm laser irradiation. 1,3-Diphenylisobenzofuran (DPBF) has a strong absorption in the visible region with a maximum absorption peak at 410 nm and a maximum fluorescence emission peak at 460 nm. Its conjugated structure could be destroyed after oxidation, resulted in disappearance of the absorption peak. As such, DPBF was selected as a singlet oxygen scavenger. Quantitative determination of the reactive oxygen species can be achieved by measuring the decrease of absorbance or quenching of fluorescence can be achieved. Therefore, this reaction is often used to quantify the ROS produced by the photosensitizer after irradiation. The formulations containing the same concentration of indocyanine green were added to the DPBF solution (10 μM), respectively, then irradiated with a laser with fixed power (1 W/cm$^2$) and wavelength. After a fixed time interval, the absorbance was measured by a microplate reader, and the irradiation time is plotted as the abscissa with the absorbance value.

Figure 6:
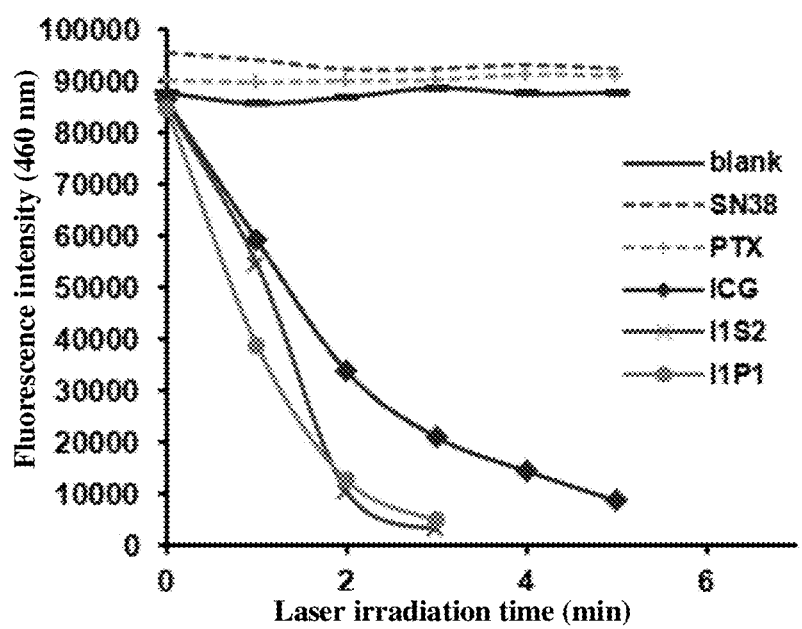
FIG. 6 is a graph showing the changes in the fluorescence intensity of DPBF for the detection of the reactive oxygen species producing rate of ICG and the complex formulation thereof.

It could be seen from FIG. 6 that the formation of either the water-soluble complex or the complex nanoparticle by interaction of ICG with small molecule drug could generate singlet oxygen more rapidly than ICG alone.

Application Embodiment 3: Photothermal Therapy Effect of Indocyanine Green Complex Formulation at the Cellular Level The endocytosis experiment was carried out with the indocyanine green complex formulations prepared in embodiments 1 and 2 of the present invention, and the free ICG was used as a control. The procedures were as follows:

The experiment was divided into ICG/SN38 group, ICG/PTX group and ICG group. The BCap37 cells on the stage of logarithmic phase were evenly seeded in a 12-well plate at 1×10$^5$ cells/well. After 24 hours of incubation, the incubation medium was discarded, and the above formulations in 1 mL culture medium were added to the plate, respectively. After 3 hours of incubation, the incubation medium was discarded, and 1 mL of PBS was added. The three wells incubated with different formulations were then irradiated with 808 nm laser for 5 min (1 W/cm$^2$), and were photographed in real time by an infrared thermal camera, and the graphs of the temperature changes of each group were recorded.

Figure 7:
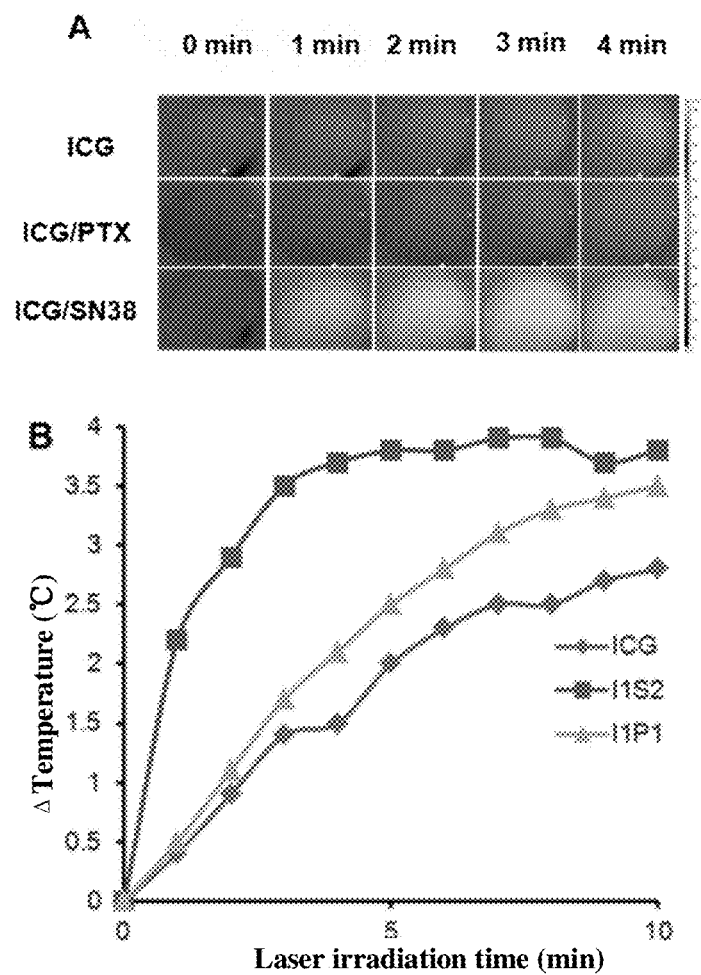
FIG. 7 is a graph showing the heating effect and corresponding temperature-time diagram of different ICG complex formulations at the cellular level.

As shown in FIG. 7, it could be seen that the cell temperature of the ICG/SN38 nanoparticles group rapidly increased, while the small molecule ICG group and the ICG/PTX aqueous solution group shown no significant temperature changes. In one aspect, the formation of nanoparticles increased the phagocytosis of the drug. In another aspect, the aggregation effect due to formation of ICG/SN38 nanoparticles made it generating more heat after absorbing the laser.

Application Embodiment 4: Photodynamic Efficacy of the Indocyanine Green Complex Formulation at the Cellular Level Similarly, the experiment was divided into ICG/SN38 complex formulation group (I2S1, I1S1, I1S2), ICG/PTX (I1P1) complex formulation group, ICG small molecule and SN38 simply mixed control group (ICG+SN38), ICG small molecule and PTX simply mixed control group (ICG+PTX) and individual ICG small molecule control group. The BCap37 cells on the stage of logarithmic phase were evenly seeded in a 12-well plate at 1×10$^5$ cells/well. After 24 hours of incubation, the original culture solution was discarded, and the above formulations in 1 mL culture medium were added to the plate, respectively. After 3 hours of incubation, the culture medium was discarded, and 2 mL of DCFH-DA that has been diluted to 10 μM was added to each well (1 μL of DCFH-DA was diluted with serum-free antibiotic-free medium with a ratio of 1:1000 to a final concentration of 10 μM). Afterwards, all wells were irradiated with 808 nm laser for 5 min (1 W/cm$^2$), placed in an incubator for 10 min, taken out and washed with the serum-free and antibiotic-free original medium three times to remove the residual extracellular DCFH-DA. The intracellular ROS generation was further quantified by the flow cytometer.

Figure 8:
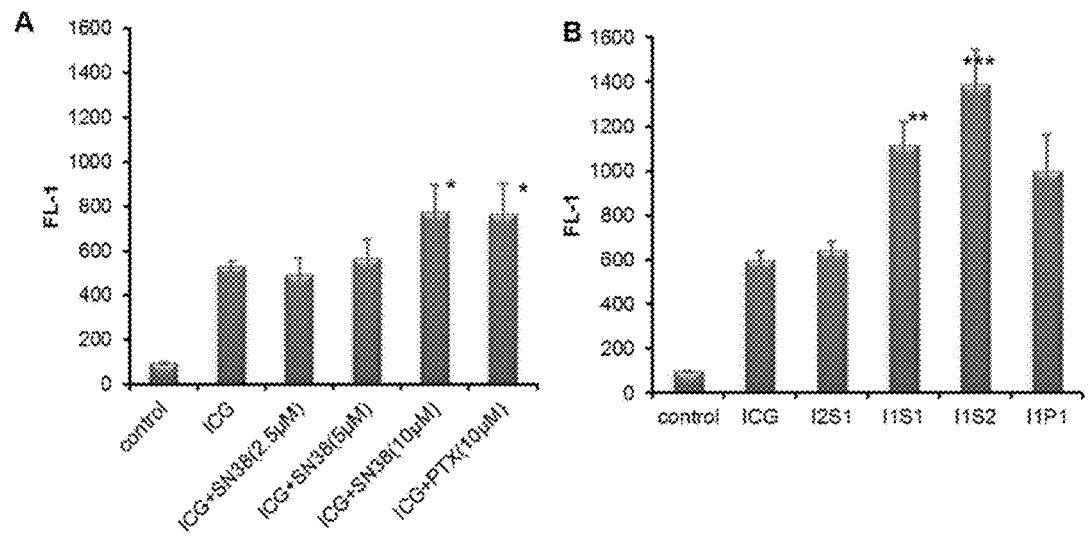
FIG. 8 is a graph showing the reactive oxygen species producing rate of different ICG complex formulations on BCap37 cells.

FIG. 8-A indicated that the simple combination of a chemotherapeutic drug and ICG could increase the sensitivity of the cells to lasers to a certain extent, while FIG. 8-B indicated that the nanoparticles formulation could significantly increase the production of ROS, compared to the usage of small molecule ICG alone ($p<0.005$).

Application Embodiment 5: Toxicity Test of the Indocyanine Green Complex Formulation at the Cellular Level 200 μL of cell suspension at the density of 4000 cells/well was uniformly added to a 96-well plate. After 24 hours of incubation, ICG, ICG/SN38 (I1S2) nanoparticles, ICG/PTX (I1P1) complex solution and ICG/CCM (I1C2) complex solution were added at different concentration points. Two identical plates were incubated in dark for 3 hours, and then culture medium was removed and washed three times with PBS, followed by addition of fresh medium. The irradiation group was further dark-incubated after 30 minutes of irradiation under a fluorescent lamp, and the other cell culture plate was dark-incubated all long as a light-proof control group. After 48 hours of incubation, culture plates were centrifuged at 900 rpm, and culture medium was carefully removed. The plates were added the medium containing 0.75 mg/mL MTT dark-incubated for 3 hours, centrifuged at 3500 rpm. After carefully removing the culture solution, the plates were added 100 μL of DMSO to each well, and shaked for 5 minutes to completely dissolve the purple solids. The absorbance (OD) value was recorded on a microplate reader. The test of each drug concentration point was repeated 3 times.

The results of the MTT assay (FIG. 9-A) indicated that the ICG in the absence of light was not toxic to the cells. However, the ICG at a concentration of 20 μM could cause the death of all the cells after irradiation, and IC$_{50}$ value of ICG with light irradiation was about 13.5 μM. The surface of the nanoparticles of I1S2 was negatively charged, which slowed down cellular uptake. Therefore, its cytotoxicity (reflected by SN38 contained in nanoparticles) was about ten times lower than that of single SN38 at the same drug concentration in the absence of light. The toxicity of the I1S2 was slightly enhanced after irradiation, yet still less toxic than pure SN38.

Figure 9:
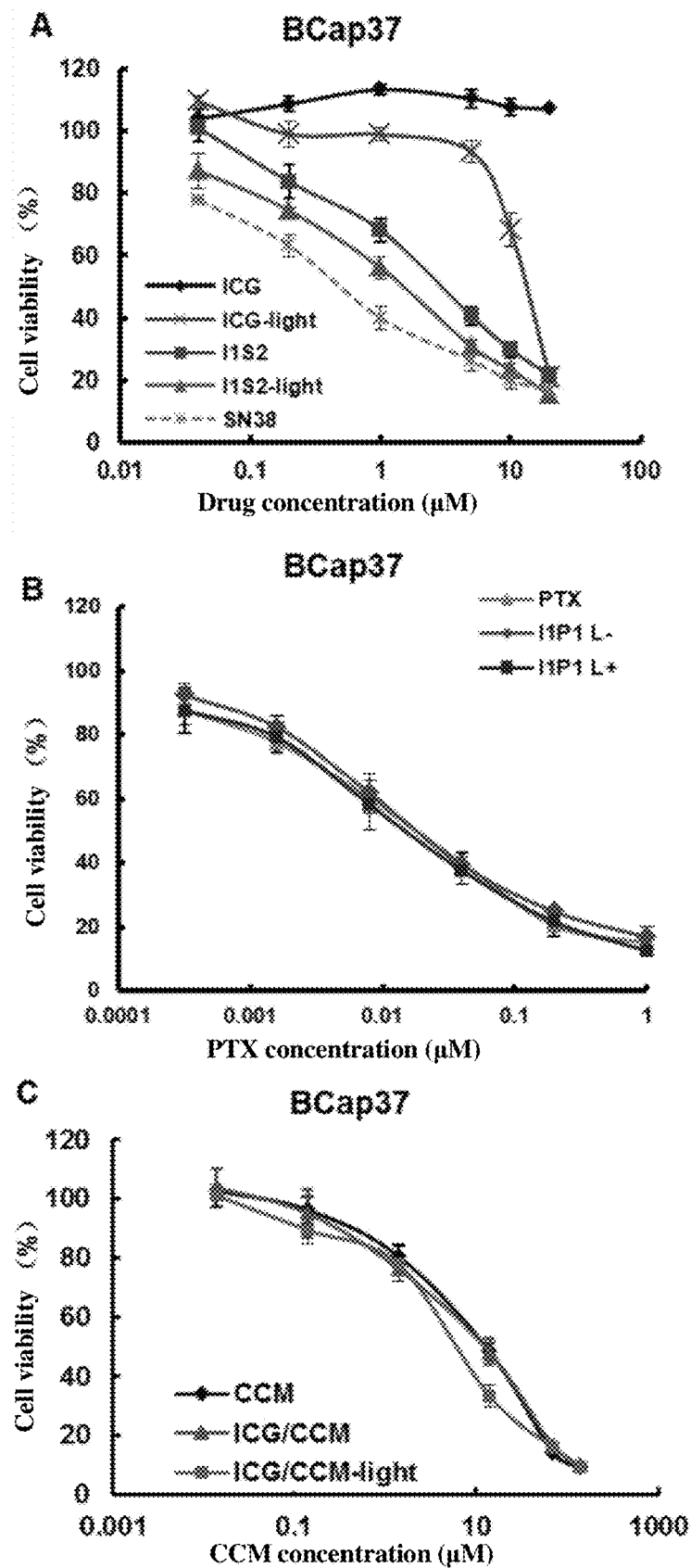
FIG. 9 is a graph showing a cytotoxicity test of ICG and the complex formulation thereof on BCap37 cells. (I1S2 is a nanoparticle formed by ICG and SN38 with a molar ratio of 1:2; and I1P1 is an aqueous solution drug of the complex formed by ICG and Paclitaxel with a molar ratio of 1:1. The drugs were applied for 24 hours and then washed off, followed by incubation for 24 hours after irradiation and non-irradiation treatment, respectively.)

FIG. 9-B indicated that the toxicity of paclitaxel (PTX) in the ICG/PTX complex formulation was unaffected, which was roughly the same as the small molecule PTX; similarly, FIG. 9-C indicated that the toxicity of CCM in the ICG/CCM complex formulation also kept at the same level as single CCM. Attributed to the property of solution formulation, drugs were individually taken up by cells, leading to no difference in the cytotoxicity. While in the case of ICG/SN38 nanoparticles formulation, the uptake rate of hydrophobic chemotherapeutic drugs was influenced due to the surface charge of the particles.

Application Embodiment 6: Plasma Clearance Test of the Indocyanine Green Complex Formulation on Mice To determine the appropriate drug ratio of ICG/SN38 nanoparticles for animal experiments, a series of ICG/SN38 nanoparticles: I2S1, I1S1, I1S2, I1S5 and I1S10 were prepared, and the average particle size thereof was 130 nm, 55 nm, 36 nm, 30 nm and 26 nm, respectively. The plasma clearance rate of the nanoparticles was measured based on the content of SN38 (10 mg/kg).

Figure 10:
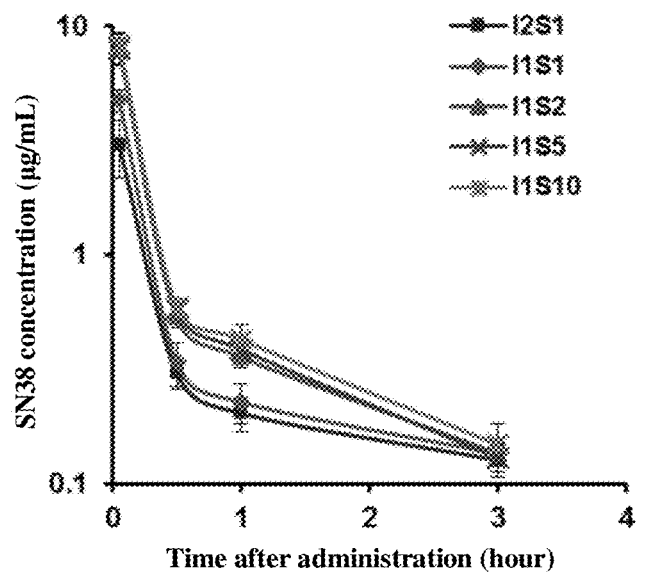
FIG. 10 is a graph showing the mice plasma clearance experiment of a series of nanoparticles with different ICG/SN38 molar ratios.

It could be seen in FIG. 10 that with the increase in SN38 proportion, the plasma clearance rate of the nanoparticles slowed down. The change was significant from I1S1 to I1S2, but it was no longer distinct for the rest groups. The reason was that when the content of SN38 was quite low, serious agglomerations of ICG were present in the solution. At this juncture, the particle size of the nanoparticles was relatively large, and the distribution was not uniform. Those large particles were quickly cleared by the body. It could be found from the atomic force microscope image (FIG. 2) that as the proportion of SN38 was increased, the particle size became smaller and more uniform.

In addition, the plasma clearance rates of small molecule ICG, ICG/PTX solutions, and ICG/SN38 nanoparticles were compared.

Figure 11:
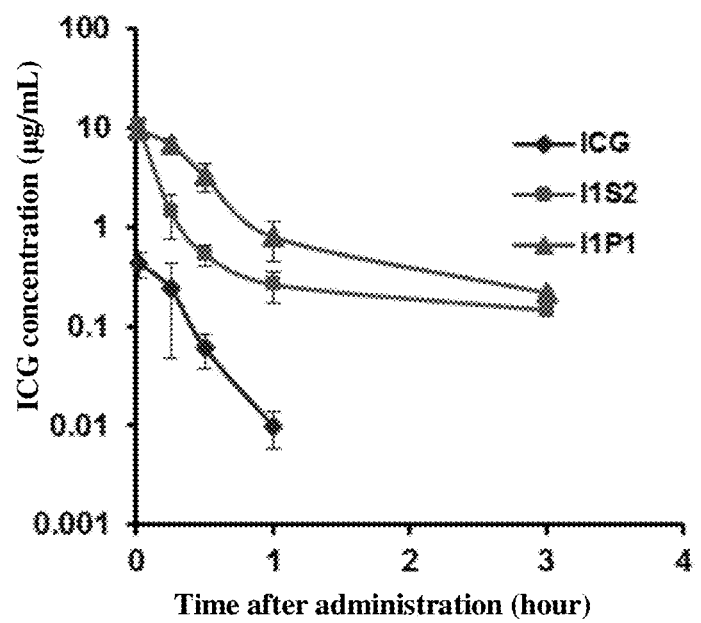
FIG. 11 is a graph showing the mice plasma clearance experiment of different ICG complex formulations and small molecule ICG.

As shown in FIG. 11, the plasma clearance of small molecule ICG was extremely fast. It was less than 1 µg/mL three minutes after injecting into the body, and ICG was nearly not detectable after 1 hour. In sharp contrast, the formation of complex nanoparticle formulation by ICG and the hydrophobic chemotherapeutic drugs significantly prolonged its blood circulation time.

Application Embodiment 7: In Vivo Imaging Experiment of ICG/SN38 Complex Formulations in Different Drug Ratios on Mice As disclosed in the plasma clearance experiments, I1S2 and I2S1 behaved significantly differently among all of the screened drug ratios groups. Therefore, these two nanoparticle formulations were further selected for in vivo fluorescence imaging in tumor-bearing nude mice, in comparison with small molecule ICG. The tumor was located 2 cm below the right armpit of the mouse, derived from BCap37 human breast cancer cell line.

Figure 12:
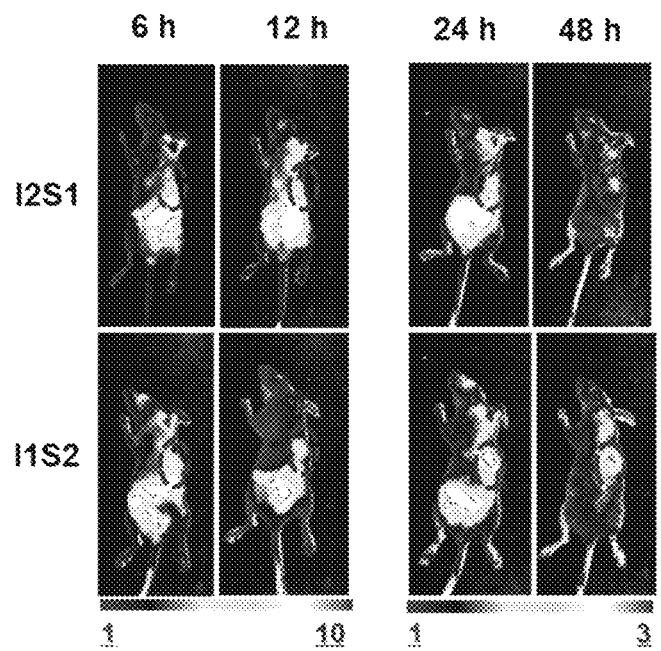
FIG. 12 is a graph showing the in vivo imaging experiment of the tumor-bearing nude mice with I1S2 and I2S1 nanocomplex formulations.

It could be obviously seen from FIG. 12 that the tumors in the I1S2 group were much brighter. Taking both the plasma clearance rate and the degree of drug enrichment in tumor into account, the I1S2 group was more suitable for the subsequent tumor inhibition experiment.

Figure 13:
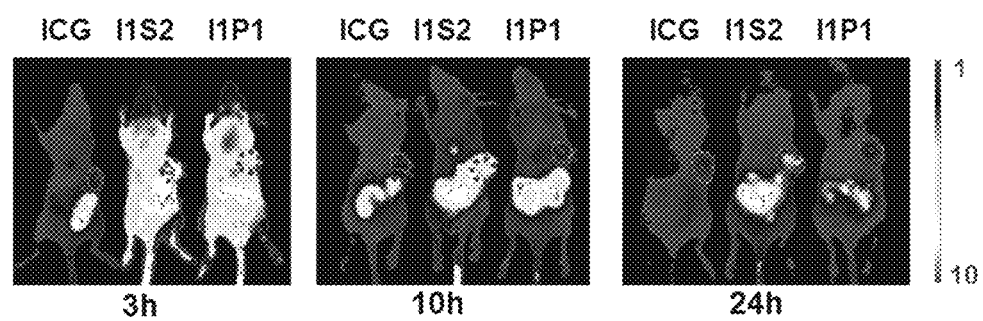
FIG. 13 is a graph showing the in vivo imaging experiment of the tumor-bearing nude mice with different ICG complex formulations and small molecule ICG.

As shown in FIG. 13, 3 hours after administration, the majority of ICG from the small molecule ICG group were cleared by the body, and the rest of the ICG was predominantly distributed in the intestine. While in the case of either ICG/SN38 nanoparticle formulation or ICG/PTX solution formulation, fluorescence was bright all over the body of the mice, especially in the liver. After 10 hours, ICG based complex formulations were eliminated. The metabolism rate was sufficiently quick to avoid the problem of cumulative toxicity. Considering the concentration of ICG in the tumor site, it was superior to prepare a complex formulation.

Application Embodiment 8: Photothermal and Synergistic Effects of the Indocyanine Green Complex Formulation on Mice After the tumor size was grown to about 100 mm³ (9 days after inoculation), the tumor-bearing nude mice were randomly divided into 7 groups, 5 in each group. One group was injected with PBS as blank control, and the other six administration groups were categorized as the ICG small molecule group without irradiation, ICG small molecule group plus irradiation, ICG/SN38 nanoparticle group, ICG/SN38 nanoparticle group plus irradiation, ICG/PTX aqueous solution group, and ICG/PTX aqueous solution group plus irradiation, respectively. The mice were injected via the tail vein at a dose of calculated ICG concentration at 10 mg/kg, and were administered once every other day for 2 times. The tumor size was recorded until the end of the experiment. The therapeutic effect was evaluated by comparing the treatment group with the control group. The tumor inhibition rate (IR) was calculated by the following formula: IR=100%×(mean tumor weight of the control group−mean tumor weight of the experimental group)/mean tumor weight of the control group.

Figure 14:
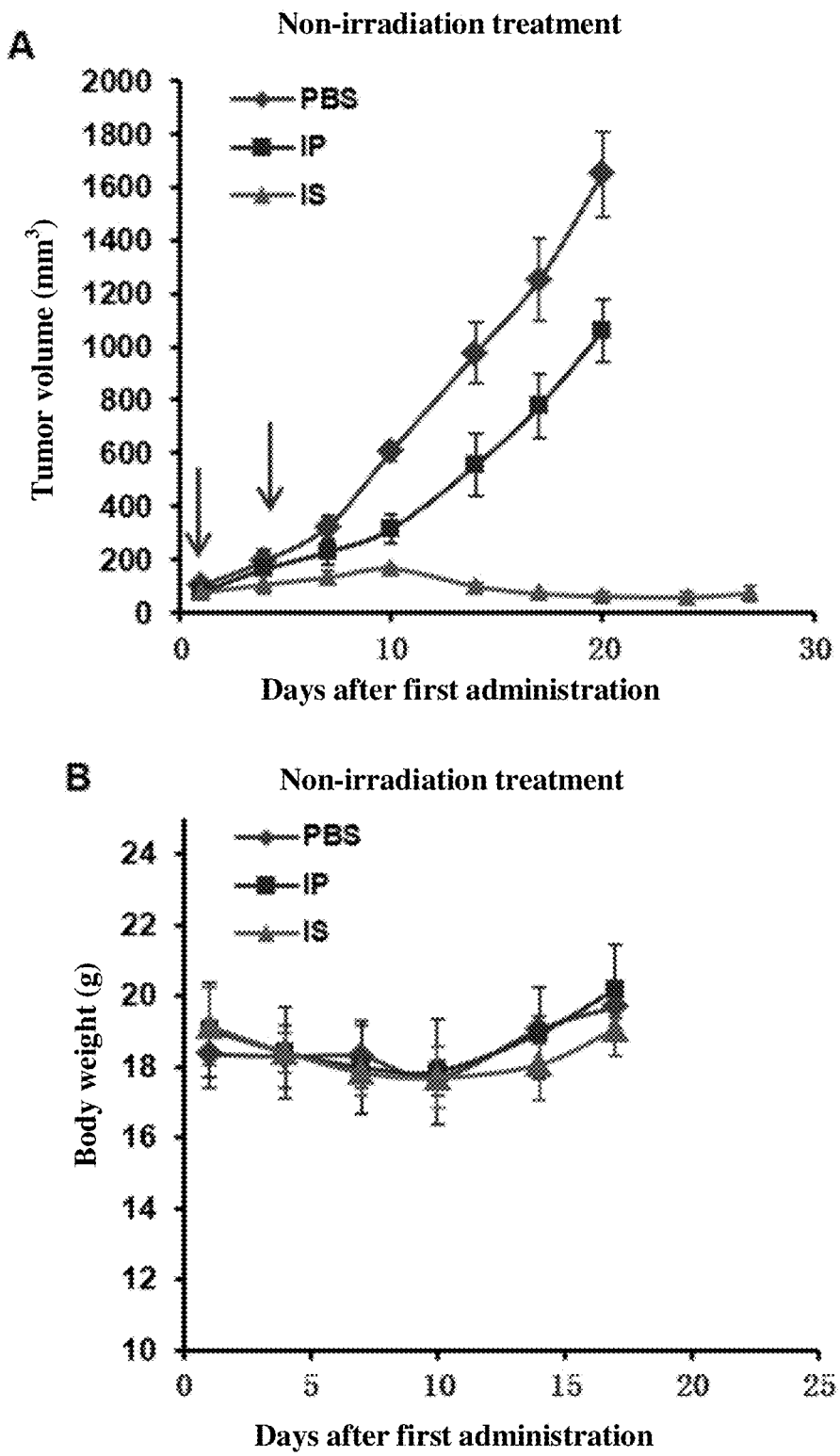
FIG. 14 is a graph showing the results of tumor inhibition experiments under non-irradiation condition. The changes in tumor volume (A) and the changes in the body weight of the nude mice (B).

FIG. 14 was the results of tumor inhibition under non-irradiation condition. The small molecule ICG displayed no anti-tumor effect at all. The ICG/PTX group was superior to the small molecule ICG group. While the ICG/SN38 nanoparticles group exhibited excellent antitumor effect. The tumor size started to decrease four days after the end of administration, and the tumor growth was suppressed for one month, after which time it began to grow again. The results indicated that upon solubilization with photosensitizer, chemotherapeutic drug alone could exert good therapeutic effect in the system.

Figure 15:
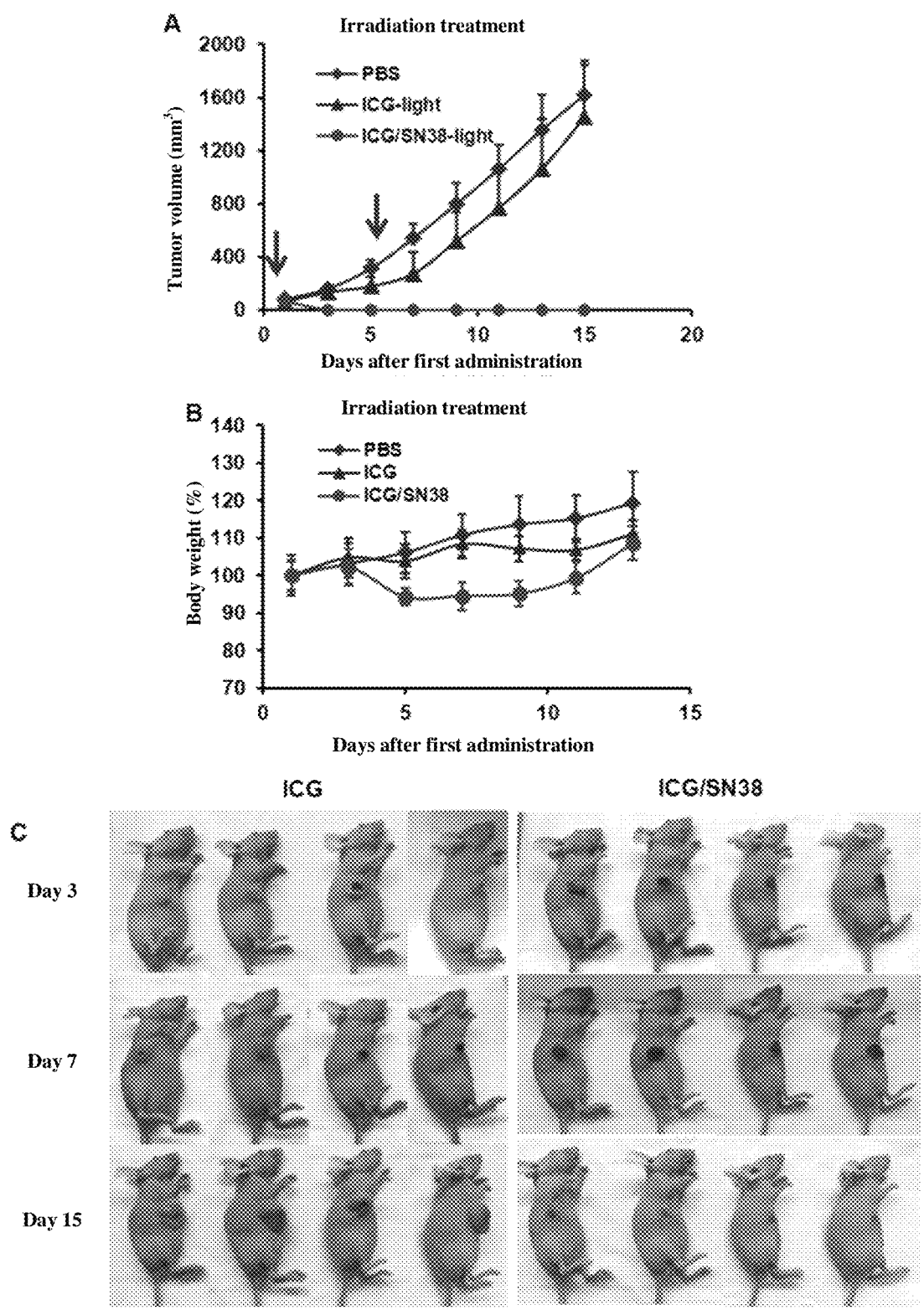
FIG. 15 is a graph showing the results of the tumor inhibition experiment under irradiation condition. The changes in tumor volume (A), the changes in the body weight of the nude mice (B) and the photographs of the nude mice taken during the period (C).

FIG. 15 was the results of tumor inhibition after irradiation treatment. The ICG group was administered twice, and the ICG/SN38 nanoparticle group was administered once. Irradiation was carried out 4 hours after administration (808 nm laser, intensity 1 W/cm², irradiation for 2 minutes). When the ICG group was irradiated, a defect appeared on the surface of the tumor but the depth was quite shallow. The residual tumors were still present and recurred rapidly after the end of treatment. However, the photosensitivity of the tumors in the nanoparticle group ICG/SN38 was greatly increased, and the whole tumor was completely eradicated. The tumor completely disappeared and there was no recurrence, suggesting that the photodynamic therapy of ICG combined with SN38 chemotherapy was significantly improved.

Figure 16:
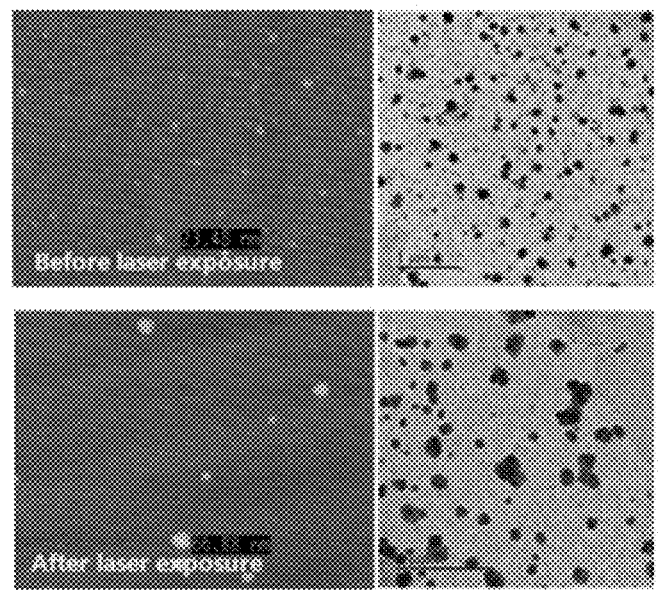
FIG. 16 is an atomic force microscopy image of the ICG/SN38 self-assembled drug-loading system nanoparticles before and after irradiation.

Application Embodiment 9: Nanoparticle Morphology of ICG/SN38 Self-Assembled Drug-Loading System It could be seen from FIG. 16 that the ICG/SN38 nanoparticles I1S5 prepared by self-assembled drug-loading system appeared in a spherical shape with size of about 25 nm, which was basically consistent with the results measured by the nanoparticle size analyzer. After irradiation, it became about twice larger, indicating that ICG played a supportive role in the formation of nanoparticles. The particles aggregated and the size became larger accompanied by the decomposition upon irradiation.

Application Embodiment 10: Drug-Loading Comparison

Figure 17:
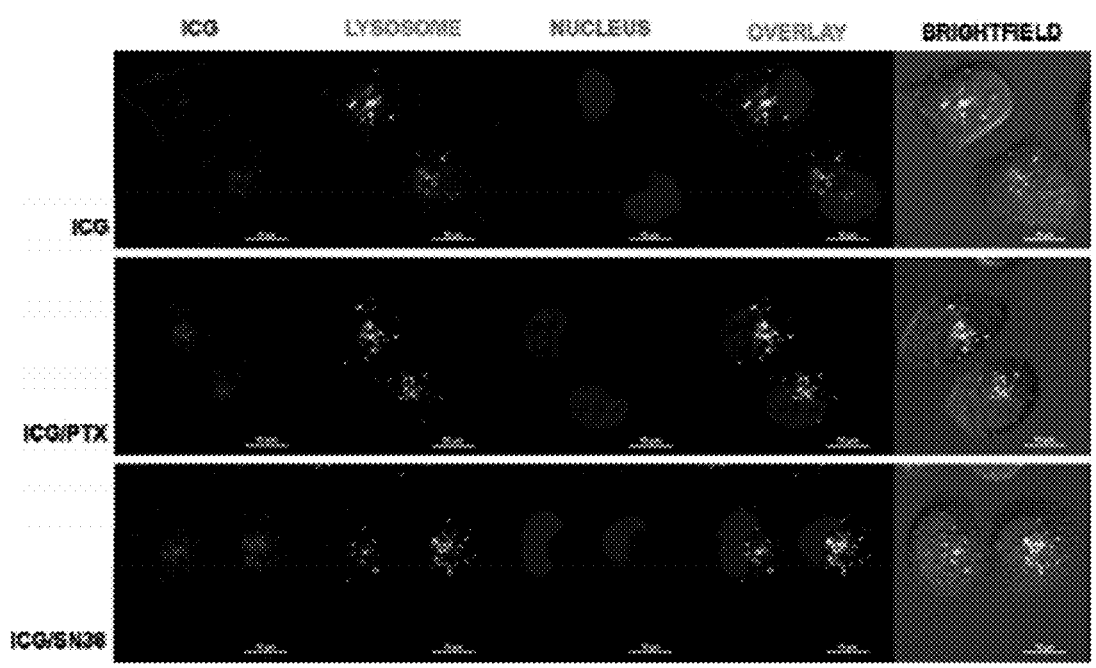
FIG. 17 is a graph of cellular uptake.

In order to judge the rate of cellular uptake of drug from the nano formulation, as well as the therapeutic effect of the drug, the laser confocal microscopy microscope was used to observe the distribution of the drug in the cells 2 hours after drug applied. As shown in FIG. 17, since ICG itself was negatively charged and the cell membrane was also negatively charged, many of the individual ICG drug substances were retained to the cell membrane and made it difficult to enter the cell. Compared to ICG group, more drugs accumulated in the lysosome from the ICG/PTX solution; In the case of ICG/SN38 nanoparticle group, the cellular uptake rate was tremendously improved, and many drugs could even enter into the cytoplasm by escaping from the lysosome. Therefore, the largest amount of ICG could enter into the cell to exert best therapeutic effect in the nano drug-loading system.

What is claimed is:

1. A self-assembled drug-loading system, wherein, the self-assembled drug-loading system comprises a hydrophilic phototherapeutic drug and a hydrophobic chemotherapeutic drug and is formed by a direct interaction between the hydrophilic phototherapeutic drug and the hydrophobic chemotherapeutic drug,
   wherein the hydrophilic phototherapeutic drug is indocyanine green,
   wherein the hydrophobic chemotherapeutic drug is 7-ethyl-10-hydroxycamptothecin, and
   wherein the hydrophilic phototherapeutic drug interacts with the hydrophobic chemotherapeutic drug to form a water-dispersible nanoparticle.

2. The self-assembled drug-loading system according to claim 1, wherein, the interaction is a π-π interaction or a hydrophobic interaction.

3. The self-assembled drug-loading system according to claim 1, wherein, the molar ratio of the hydrophilic phototherapeutic drug to the hydrophobic chemotherapeutic drug in the self-assembled drug-loading system is from 2:1 to 1:10.

4. The self-assembled drug-loading system according to claim 3, wherein, the molar ratio of the hydrophilic phototherapeutic drug to the hydrophobic chemotherapeutic drug in the self-assembled drug-loading system is 2:1, 1:1, 1:2, 1:5 or 1:10.

5. A process for treating tumor in a subject in need thereof, comprising: administering an effective amount of the self-assembled drug-loading system according to claim 1 to the subject.

6. A preparation method for a self-assembled drug-loading system, comprising the following steps:
   (1) dissolving the hydrophilic phototherapeutic drug and the hydrophobic chemotherapeutic drug of claim 1 in an organic solvent;
   (2) adding an aqueous solution.

7. A preparation method for a complex formulation, comprising the following steps:
   (1) dissolving the hydrophilic phototherapeutic drug and the hydrophobic chemotherapeutic drug of claim 1 in an organic solvent;
   (2) adding an aqueous solution to form a water-soluble complex or nanoparticles;
   (3) removing the organic solvent to obtain an aqueous solution formulation or further lyophilizing to prepare a lyophilized powder formulation.

8. The preparation method for a complex formulation according to claim 7, wherein, the organic solvent is selected from the group consisting of DMSO, DMF, THF, methanol, ethanol and isopropanol.

9. The preparation method for a complex formulation according to claim 7, the aqueous solution is selected from the group consisting of pure water, physiological saline, 5 wt. % glucose solution and phosphate buffer.

* * * * *